United States Patent
Bernegger et al.

(12)

(10) Patent No.: US 6,252,112 B1
(45) Date of Patent: Jun. 26, 2001

(54) PROCESS FOR THE PREPARATION OF AN ENANTIOMER OF A (1R, 4S) OR (1S, 4R)-1-AMINO-4-(HYDROXYMETHYL)-2-CYCLOPENTENE DERIVATIVE

(75) Inventors: Christine Bernegger, Münster; Eva Maria Urban; Olwen Mary Birch, both of Visp; Kurt Burgdorf, Ried-Brig; Frank Brux, Raron; Kay-Sara Etter, Niedergampel; Pierre Bossard, Onex; Walter Brieden, Brig-Glis; Laurent Duc, Chermignon; John Gordon, Naters; Colm O'Murchu, Visp; Yves Guggisberg, Sierre, all of (CH)

(73) Assignee: Lonza A.G.,, Basel (CH)

( * ) Notice: Subject to any disclaimer, the term of this patent is extended or adjusted under 35 U.S.C. 154(b) by 0 days.

(21) Appl. No.: 09/373,857

(22) Filed: Aug. 13, 1999

Related U.S. Application Data

(62) Division of application No. 09/073,553, filed on May 6, 1998, now Pat. No. 6,156,893.

(30) Foreign Application Priority Data

| May 13, 1997 | (CH) | ................................................. 1116/97 |
| Nov. 27, 1997 | (CH) | ................................................. 2740/97 |

(51) Int. Cl.$^7$ ................................................. C07C 231/18
(52) U.S. Cl. ..................... 564/217; 435/128; 435/129; 560/115; 564/186; 564/210; 564/216
(58) Field of Search ................................. 435/128, 129; 560/115; 564/186, 210, 216, 217

(56) References Cited

U.S. PATENT DOCUMENTS 5,371,282 12/1994 Nohira et al. .................. 562/401

FOREIGN PATENT DOCUMENTS

| 0508352 | 10/1992 | (EP). |
| 9404486 | 3/1994 | (WO). |
| 9521161 | 8/1995 | (WO). |

OTHER PUBLICATIONS

Luis E. Martinez et al., "Highly Efficient Enantioselective Synthesis of Carbocyclic Nucleoside Analogs Using Selective Early Transition Metal Catalysis," J. Org. Chem. 1996 vol. 61, pp. 7963–66.

Michael T. Crimmins et al., "An Efficient Asymmetric Approach to Carbocyclic Nucleosides: Asymmetric Synthesis of 1259089, a Potent Inhibitor of HIV Reverse Transcriptase," J. Org. Chem. 1996, vol. 61, pp. 4,192–93.

Jeffrey Campbell et al., "Chirospecific Synthesis and Precursors of Cyclopentene and Cyclopentene Carbocyclic Nucleosides by [3+3]–Coupling and Transannular Alkylation," J. Org. Chem. 1995, vol. 60, pp. 4602–4616.

Primary Examiner—Richard L. Raymond
(74) Attorney, Agent, or Firm—Baker Botts, L.L.P.

(57) ABSTRACT

A novel process for the preparation of (1S, 4R)- or (1R, 4S)-4-(2-amino-6-chloro-9H-purin-9-yl)-2-cyclopentene-1-methanol of the formula

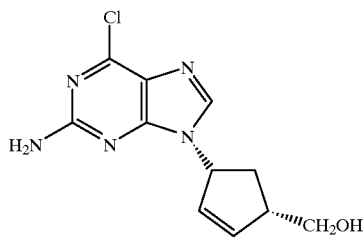

I

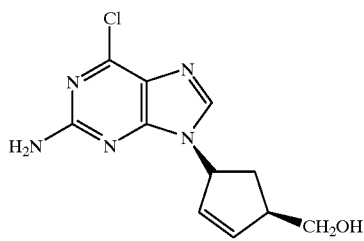

II is described.

1 Claim, 2 Drawing Sheets

PROCESS FOR THE PREPARATION OF AN ENANTIOMER OF A (1R, 4S) OR (1S, 4R)-1-AMINO-4-(HYDROXYMETHYL)-2-CYCLOPENTENE DERIVATIVE

This is a divisional of U.S. application Ser. No. 09/073,553, filed May 6, 1998, now U.S. Pat. No. 6,156,893.

The invention relates to a novel process for the preparation of (1S, 4R)- or (1R, 4S)-4-(2-amino-6-chloro-9H-purin-9-yl)-2-cyclopentene-1-methanol of the formulae

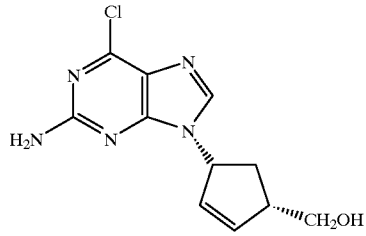

I

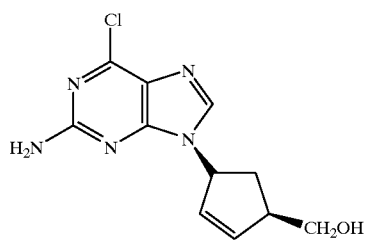

II and to a novel process for preparing optically active compounds of the general formulae

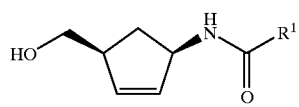

XVI

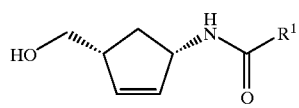

XVII (1S, 4R)-4-(2-Amino-6-chloro-9H-purin-9yl)-2-cyclopentene-1-methanol is an important intermediate for preparing 2-aminopurine nucleosides such as, for example, for preparing (1S, 4R)-4-[2-amino-6-(cyclopropylamino)-9H-purin-9yl]-2-cyclopentene-1-methanol (WO 95/21 161) or for preparing 1592U89 (J. Org. Chem., 1996, 61, 4192–4193; J. Org. Chem., 1996, 61, 7963–7966).

A process for preparing (1S, 4R)-4-(2-amino-6-chloro-9H-purin-9-yl)-2-cyclopentene-1-methanol starting from (1S, 4R)-4-amino-2-cyclopentene-1-methanol is described in WO 95/21 161. The disadvantage of this process is that the precursor (1S, 4R)-4-amino-2-cyclopentene-1-methanol can be obtained only via (±)-2-azabicyclo[2.2.1]hept-5-en-3-one substituted by the costly BOC protective group (tert-butyloxycarbonyl protective group) (J. Org. Chem., 1995, 60, 4602–4616).

The object of the invention was to provide a simple, low-cost and more economical process for preparing (1S, 4R)- or (1R, 4S)-4-(2-amino-6-chloro-9H-purin-9-yl)-2-cyclopentene-1-methanol.

This object has been achieved by the novel process according to claim 1.

The first stage in the novel process is carried out by acylating (±)-2-azabicyclo[2.2.1]hept-5-en-3-one of the formula

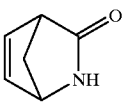

III to give a (±)-2-azabicyclo[2.2.1]hept-5-en-3-one derivative of the general formula

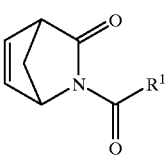

IV in which $R^1$ denotes $C_{1-4}$-alkyl, $C_{1-4}$-alkoxy, aryl or aryloxy.

$C_{1-4}$-Alkyl can be substituted or unsubstituted. Substituted $C_{1-4}$-alkyl means hereinafter $C_{1-4}$-alkyl substituted by a halogen atom. F, Cl, Br or I can be used as halogen atom. Examples of $C_{1-4}$-alkyl are methyl, ethyl, propyl, butyl, isobutyl, tert-butyl, isopropyl, chloromethyl, bromomethyl, dichloromethyl, dibromomethyl. Preferably used as $C_{1-4}$-alkyl is methyl, ethyl, propyl, butyl, isobutyl or chloromethyl.

It is possible to use as $C_{1-4}$-alkoxy, for example, methoxy, ethoxy, propoxy, butoxy, tert-butoxy or isobutoxy. The $C_{1-4}$-alkoxy preferably used is tert-butoxy.

It is possible to use as aryl, for example, phenyl or benzyl, preferably phenyl. Benzyloxy or phenoxy, for example, can be used as aryloxy.

The precursor (±)-2-azabicyclo[2.2.1]hept-5-en-3-one can be prepared as disclosed in EP-A 0 508 352.

The acylation can be carried out with a carbonyl halide of the general formula

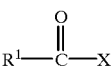

XI or with a carboxylic anhydride of the general formula

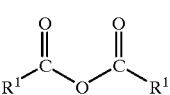

XII in which $R^1$ has the stated meaning, and X denotes a halogen atom. F, Cl, Br or I can be used as halogen atom. Cl or F is preferably used.

Examples of carbonyl halides are: acetyl chloride, chloroacetyl chloride, butyryl chloride, isobutyryl chloride, phenylacetyl chloride, benzyl chloroformate (Cbz—Cl), propionyl chloride, benzoyl chloride, allyl chloroformate or tert-butyloxycarbonyl fluoride. Examples of carboxylic anhydrides are: di-tert-butyl dicarbonate, butyric anhydride, acetic anhydride or propionic anhydride.

The acylation can be carried out without solvent or with an aprotic solvent.

The acylation is expediently carried out in an aprotic solvent. Examples of suitable aprotic solvents are diisopropyl ether, pyridine, acetonitrile, dimethyl-formamide, triethylamine, tetrahydrofuran, toluene, methylene chloride, N-methylpyrrolidone or mixtures thereof.

The acylation is expediently carried out at a temperature from −80 to 50° C., preferably from 0 to 25° C.

In the second stage of the novel process, the (±)-2-azabicyclo[2.2.1]hept-5-en-3-one derivative of the formula IV is reduced to give a cyclopentene derivative of the general formula

V in which $R^1$ has the stating meaning.

The reduction is expediently carried out with an alkali metal borohydride or alkaline earth metal borohydride, with an alkali metal aluminium hydride or alkaline earth metal aluminium hydride or with Vitride (sodium bis(2-methoxyethoxy)aluminium hydride). Sodium or potassium aluminium hydride can be used as alkali metal aluminium hydride. Sodium or potassium borohydride can be used as alkali metal borohydride. Calcium borohydride can be used as alkaline earth metal borohydride. Aluminium nitride for example can be used as nitride.

The reduction is expediently carried out in a protic solvent. Protic solvents which can be used are lower aliphatic alcohols such as methanol, ethanol, propanol, isopropanol, butanol, sec-butanol, tert-butanol, isobutanol or water, or a mixture of the said alcohols and water.

The reduction is expediently carried out at a temperature from −40 to 40° C., preferably from 0 to 20° C.

The third stage in the novel process, the conversion of the cyclopentene derivative of the general formula V into the (1R, 4S)- or (1S, 4R)-1-amino-4-(hydroxymethyl)-2-cyclopentene of the formulae

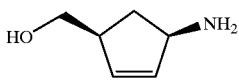

VI

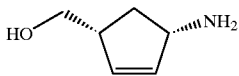

VII is carried out either by means of microorganisms or of an enzyme having N-acetylamino-alcohol hydrolase activity or by means of penicillin G acylases. This biotransformation converts the acylated (1S, 4R)- or (1R, 4S)-amino alcohol derivative to result in the (1R, 4S) or (1S, 4R)-1-amino-4-(hydroxymethyl)-2-cyclopentene (formula VI, VII).

All microorganisms which utilize a cyclopentene derivative of the general formula V as sole nitrogen source, as sole carbon source or as sole carbon and nitrogen source are suitable for the biotransformation. The microorganisms can be isolated from soil samples, sludge or waste water with the assistance of conventional microbiological techniques. The microorganisms are isolated by culturing them in a nutrient medium containing a cyclopentene derivative of the general formula

V in which $R^1$ has the stated meaning,
as sole carbon and nitrogen source
as sole nitrogen source with a suitable carbon source a
as sole carbon source with a suitable nitrogen source,
in a conventional way.

Examples of suitable cyclopentene derivatives of the general formula V are: N-acetyl-, N-propionyl-, N-isobutyryl-, N-tert-butoxycarbonyl-(N-BOC), N-butyryl- or N-phenylacetyl-1-amino-4-hydroxymethyl-2-cyclopentene.

The microorganisms can use as suitable nitrogen source, for example, ammonium, nitrates, amino acids or ureas as substrate for growth. The microorganisms can use as suitable carbon source, for example, sugars, sugar alcohols, $C_2$–$C_4$-carboxylic acids or amino acids as substrate for growth. Hexoses such as glucose or pentoses can be used as sugars. Glycerol, for example, can be used as sugar alcohol. Acetic acid or propionic acid can be used, for example, as $C_2$–$C_4$-carboxylic acids. Leucine, alanine, asparagine can be used, for example, as amino acids.

The selection medium and culture medium which can be used are those conventional among those skilled in the art, such as, for example, the one described in Table 1 or a complete medium (medium containing yeast extract) such as, for example, nutrient yeast broth (NYB), preferably using the one described in Table 1.

During the culturing and selection, the active enzymes of the microorganisms are expediently induced. The cyclopentene derivatives of the general formula V can be used as enzyme inducer.

The culturing and selection normally takes place at a temperature from 20° C. to 40° C., preferably from 30° C. to 38° C. and at a pH between pH 5.5 and pH 8, preferably between pH 6.8 and pH 7.8.

The biotransformation is expediently carried out with microorganisms which utilize the (1R, 4S) isomer of the cyclopentene derivative as sole carbon source, as sole carbon and nitrogen source or as sole nitrogen source.

The biotransformation is preferably carried out by means of microorganisms of the genus Alcaligenes/Bordetella, Rhodococcus, Arthrobacter, Alcaligenes, Agrobacterium/Rhizobium, Bacillus, Pseudomonas or Gordona, in particular of the species Alcaligenes/Bordetella FB 188 (DSM 11172), *Rhodococcus erythropolis* CB 101 (DSM 10686), *Arthrobacter sp.* HSZ5 (DSM 10328), *Rhodococcus sp.* FB 387 (DSM 11291), *Alcaligenes xylosoxydans ssp. denitrificans* HSZ17 (DSM 10329), Agrobacterium/Rhizobium HSZ30, *Bacillus simplex* K2, *Pseudomonas putida* K32 or *Gordona sp.* CB 100 (DSM 10687), and with their functionally equivalent variants and mutants. Deposition in accordance with the Budapest Treaty at the Deutsche Sammlung von Midroorganismen und Zellkulturen GmbH, Mascheroderweg 1b, D38124 Braunschweig, took place on May 20, 1996 for the microorganisms DSM 10686 and 10687, on Nov. 6, 1995 for the microorganisms DSM 10328 and DSM 10329, on Oct. 8, 1996 for the microorganism DSM 11291 and on Sep. 20, 1996 for the microorganism DSM 11172.

"Functionally equivalent variants and mutants" mean microorganisms having essentially the same properties and functions as the original microorganisms. Variants and mutants of the type can be produced by chance, for example by UV radiation.

Taxonomic description of Alcaligenes/Bordetella FB 188 (DSM 11172)

| Cell form | rods |
|---|---|
| Width μm | 0.5–0.6 |
| Length μm | 1.0–2.5 |
| Motility | + |
| Flagellation | peritrichous |
| Gram reaction | – |
| Lysis by 3% KOH | + |
| Aminopeptidase (Cerny) | + |
| Spores | – |
| Oxidase | + |
| Catalase | + |
| ADH (alcohol dehydrogenase) | – |
| $NO_2$ from $NO_3$ | – |
| Denitrification | – |
| Urease | – |
| Hydrolysis of gelatin | – |
| Acid from (OF test): | |
| Glucose | – |
| Fructose | – |
| Arabinose | – |
| Adipate | + |
| Caprate | + |
| Citrate | + |
| Malate | + |
| Mannitol | – |

Taxonomic description of *Rhodococcus erythropolis* CB 101 (DSM 106 86)

1. Morphology and color of the colonies: short branched hyphae which, when old, disintegrate into rods and cocci, colonies glistening and partly confluent, beige with pink tinge. RAL 1001;
2. Diagnosed amino acid of the peptidoglycan; mesodiaminopimelic acid;
3. Mycolic acids: Rhodococcus mycolic acids; determination of the mycolic acid chain length ($C_{32}$–$C_{44}$) and comparison of the data with the entries in the DSM mycolic acid data bank revealed very great similarity with the patterns of the *Rhodococcus erythropolis* strains (similarity 0.588).
4. Fatty acid pattern: unbranched, saturated and unsaturated fatty acids plus tuberculostearic acid.
5. On partial sequencing of the 16S rDNA of the strain, a high level of agreement (100%) was found with the sequences of the specific regions of *Rhodococcus erythropolis*.

The identification result is unambiguous because three mutually independent methods (mycolic acids, fatty acids, 16S rDNA) have assigned the strain to the species *Rhodococcus erythropolis*.

Taxonomic description of *Gordona sp.* CB 100 (DSM 10687)

1. Morphology and color of the colonies: short branched hyphae which, when old, disintegrate into rods and cocci, colonies pale orange, (RAL 2008);
2. Diagnosed amino acid of the peptidoglycan: mesodiaminopimelic acid;
3. Menaquinone pattern: MK-9 ($H_2$) 100%;
4. Mycolic acids: Gordona mycolic acids; the mycolic acid chain length ($C_{50}$–$C_{60}$) was determined by high temperature gas chromatography. This pattern corresponds to the pattern found in representatives of the genus Gordona.
5. Fatty acid pattern: unbranched, saturated and unsaturated fatty acids plus tuberculostearic acid.
6. On partial sequencing of the 16S rDNA of the strain, only a relatively low agreement of 98.8% could be found with the sequences of the specific regions of *Gordona rubropertincta*.

On the basis of the available results (menaquinones, mycolic acids, fatty acids, 16S rDNA), although the isolate can be unambiguously assigned to the genus Gordona it is not possible on the basis of the results to make an assignment to a known *Gordona species*. It is therefore to be assumed that the strain DSM 10687 is a new and previously undescribed species of the genus Gordona.

Taxonomic description of *Alcaligenes xylosoxydans ssp. denitrificans* HSZ 17 (DSM 10329)

Properties of the strain

| Cell form | rods |
|---|---|
| Width μm | 0.5–0.6 |
| Length μm | 1.5–3.0 |
| Motility | + |
| Flagellation | peritrichous |
| Gram reaction | – |
| Lysis by 3% KOH | + |
| Aminopeptidase (Cerny) | + |
| Spores | – |
| Oxidase | + |
| Catalase | + |
| Anaerobic growth | – |
| ADK (alcohol dehydrogenase) | + |
| $NO_2$ from $NO_3$ | + |
| Denitrification | + |
| Urease | – |
| Hydrolysis of | |
| Gelatin | – |
| Tween 80 | – |
| Acid from (OF test): | |
| Glucose aerobic | – |
| Xylose 80 | – |
| Substrate utilization | |
| Glucose | – |
| Fructose | – |
| Arabinose | – |
| Citrate | + |
| Malate | + |
| Mannitol | – |

Taxonomic description of *Arthrobacter sp.* HSZ5 (DSM 10328)

| Characterization: | Gram-positive irregular rods with a pronounced rod-cocci growth cycle; strictly aerobic; no acid or gas formation from glucose. |
|---|---|
| Motility | – |
| Spores | – |
| Catalase | + | meso-Diaminopimelic acid in the cell wall: no Peptidoglkycan type: A3α, L-Lys-L-Ser-L-Thr-L-Ala

| 16S rDNA sequence similarity: | The highest values found on sequencing the region |
|---|---|

Taxonomic description of Agrobacterium/Rhizobium HSZ30

| Cell form | pleomorphic rods |
|---|---|
| Width [μm] | 0.6–1.0 |
| Length [μm] | 1.5–3.0 |
| Gram reaction | − |
| Lysis by 3% KOH | + |
| Aminopeptidase | + |
| Spores | − |
| Oxidase | + |
| Catalase | + |
| Motility | + |
| Anaerobic growth | − |
| Nitrite from nitrate | − |
| Denitrification | − |
| Urease | + |
| Hydrolysis of gelatin | − |
| Acid from: | |
| L-Arabinose | + |
| Galactose | − |
| Melezitose | − |
| Fucose | + |
| Arabitol | − |
| Mannitol | − |
| Erythritol | − |
| Alkalinization of litmus milk | + |
| Ketolactose | − |

Partial sequencing of the 16S rDNA revealed comparably large similarities of about 96% with representatives of the genera Agrobacterium and Rhizobium. Unambiguous assignment to a species described within these genera is not possible.

Taxonomic description of *Bacillus simplex* K2

| Cell form | rods |
|---|---|
| Width [μm] | 0.8–1.0 |
| Length [μm] | 3.0–5.0 |
| Spores | − |
| Ellipsoidal | − |
| Circular | − |
| Sporangium | − |
| Catalase | + |
| Anaerobic growth | − |
| VP reaction | n.g. |
| Maximum temperature | |
| Growth positive at ° C. | 40 |
| Growth negative at ° C. | 45 |
| Growth in medium pH 5.7 | − |
| NaCl | |
| 2% | + |
| 5% | − |
| 7% | − |
| 10% | − |
| Lysozyme medium | + |
| Acid from (ASS) | |
| D-Glucose | + |
| L-Arabinose | + |
| D-Xylose | − |
| D-Mannitol | + |
| D-Fructose | + |
| Gas from fructose | − |
| Lecithinase | − |
| Hydrolysis of | |
| Starch | + |
| Gelatin | + |
| Casein | − |
| Tween 80 | + |
| Aesculin | − |
| Utilization of | |
| Citrate | + |
| Propionate | − |
| Nitrite from nitrate | + |
| Indole | − |
| Phenylalanine deaminase | − |
| Arginine dihydrolase | − |

Analysis of the cellular fatty acids yielded confirmation of the assignment to the genus Bacillus.

Partial sequencing of the 16S rDNA revealed a similarity of 100% with Bacillus simplex.

Taxonomic description of *Pseudomonas putida* K32

| Cell form | rods |
|---|---|
| Width [μm] | 0.8–0.9 |
| Length [μm] | 1.5–4.0 |
| Motility | + |
| Flagellation | polar >1 |
| Gram reaction | − |
| Lysis by 3% KOH | + |
| Aminopeptidase | + |
| Spores | − |
| Oxidase | + |
| Catalase | + |
| Anaerobic growth | − |
| Pigments | |
| fluorescent | + |
| Pyocyanin | − |
| ADH | + |
| Nitrite from nitrate | − |
| Denitrification | − |
| Urease | − |
| Hydrolysis of gelatin | − |
| Substrate utilization | |
| Adipate | − |
| Citrate | + |
| Malate | + |
| D-Mandelate | + |
| Phenylacetate | + |
| D-Tartrate | − |
| D-Glucose | + |
| Trehalose | − |
| Mannitol | − |
| Benzoylformate | − |
| Propylene glycol | + |
| Butylamine | + |
| Benzylamine | + |
| Tryptamine | − |
| Acetamide | + |
| Hippurate | + |

The profile of cellular fatty acids is typical of *Pseudomonas putida*.

Partial sequencing of the 16S rDNA revealed similarities of about 98% with *Pseudomonas mendocina* and *Pseudomonas alcaligenes*. The similarity with *Pseudomonas putida* was 97.4%.

Taxonomic description of Rhodococcus sp. FB 387 (DSM 11291)

1. Morphology and colour of the colonies: short branched hyphae which, when old, disintegrate to rods and cocci, colonies matt, pale red-orange RAL 2008;
2. Diagnosed amino acid of the peptidoglycan: mesodiaminopimelic acid;
3. Mycolic acids: *Rhodococcus mycolic* acids; Determination of the mycolic acid chain length ($C_{32}$–$C_{44}$) and comparison of the data with the entries in the DSMZ mycolic acid data bank revealed only very small similarity with the patterns of *Rhodococcus ruber* strains (similarity 0.019). This correlation factor is too low to be used for species identification.
4. Fatty acid pattern: unbranched, saturated and unsaturated fatty acids plus tuberculostearic acid.

This fatty acid pattern is diagnostic for all representatives of the genus Rhodococcus and its close relatives such as Mycobacterium, Nocardia and Gordona. An attempt was made by including the qualitative and quantitative differences in the fatty acid pattern to carry out a differentiation to the species level. Numerical methods were used to compare the fatty acid pattern of Rhodococcus sp. FB 387 with the entries in the data bank. It was not possible with this method either to assign Rhodococcus sp. FB 387, because of the small similarity (0.063), to any described Rhodococcus species.
5. On partial sequencing of the 16S rDNA of the strain, 96–818 was assigned to *Rhodococcus opacus* with a correlation of 97.9%. This sequence agreement is far below that of 99.5% required for unambiguous species assignment in this taxon.

On the basis of the available results, it can be assumed that the strain Rhodococcus sp. FB 387 is a new and not previously described Rhodococcus species.

The biotransformation can be carried out, after conventional initial cultivation of these microorganisms, with quiescent cells (non-growing cells no longer requiring a carbon and energy source) or with growing cells. The biotransformation is preferably carried out with quiescent cells.

The enzymes with N-acetylamino-alcohol hydrolase activity which are suitable for the biotransformation can be isolated from the described microorganism cells for example by disruption as usual in the art. It is possible to use for this for example the ultrasound or French press method. These enzymes are preferably isolated from the microorganisms of *Rhodococcus erythropolis* CB101 (DSM 10686).

Suitable penicillin G acylases are obtained from many microorganisms such as, for example, bacteria or actinomycetes, specifically from the following microorganisms: *Escherichia coli* ATCC 9637, *Bacillus megaterium*, *Streptomyces lavendulae* ATCC 13664, *Nocardia sp.* ATCC 13635, *Providencia rettgeri* ATCC 9918, *Arthrobacter viscosus* ATCC 15294, *Rhodococcus fascians* ATCC 12975, *Streptomyces phaeochromogenes* ATCC 21289, Achromobacter ATCC 23584 and *Micrococcus roseus* ATCC 416. Penicillin G acylases which can be bought are used in particular, such as penicillin G acylase EC 3.5.1.11 from *E. coli* (Boehringer Mannheim) or from *Bacillus megaterium*.

Immobilized penicillin G acylases are used in a preferred embodiment.

The biotransformation can be carried out in media usual in the art, such as, for example, in low-molarity phosphate, citrate or Hepes buffer, in water, complete media such as, for example, Nutrient Yeast Broth (NYB) or in that described in the table. The biotransformation is preferably carried out in the medium shown in Table 1 or in low-molarity phosphate buffer.

The biotransformation is expediently carried out with a single or continuous addition of the cyclopentene derivative (formula V) so that the concentration does not exceed 10% by weight, preferably 2% by weight.

The pH during the biotransformation can be in a range from 5 to 9, preferably from 6 to 8. The biotransformation is expediently carried out at a temperature from 20 to 40° C., preferably from 25 to 30° C.

In the fourth stage, the cyclopentene derivative (formula VI or VII) is converted with N-(2-amino-4,6-dichloro-5-pyrimidinyl)formamide of the formula

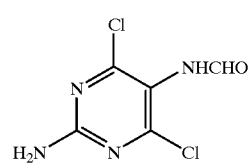

VIII into the (1S,4R)- or (1R,4S)-4-[(2-amino-6-chloro-5-formamido-4-pyrimidinyl)amino]-2-cyclopentene-1-methanol of the formula IX or X

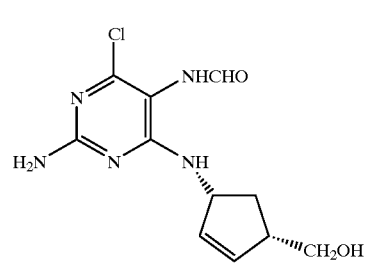

IX

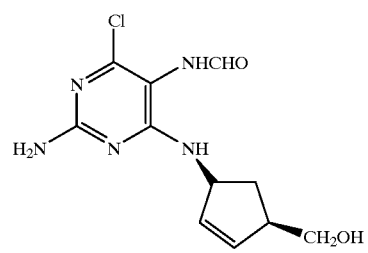

X

The N-(2-amino-4,6-dichloro-5-pyrimidinyl)formamide can be prepared as disclosed in WO 95/21 161.

The reaction in the fourth stage is expediently carried out in the presence of a base. Organic bases or inorganic bases can be employed as base. Trialkylamines can be used as organic bases. Examples of trialkylamines used are triethylamine, tributylamine, tribenzylamine, pyridine or N-methylpyrrolidine. Examples of inorganic bases which can be employed are alkali metal or alkaline earth metal carbonates or alkali metal or alkaline earth metal bicarbonates such as, for example, potassium carbonate and sodium bicarbonate.

The reaction in the fourth stage is expediently carried out in a protic solvent. Lower aliphatic alcohols such as methanol, ethanol, propanol, isopropanol, butanol or isobutanol can be used as protic solvent.

The reaction in the fourth stage is expediently carried out at a temperature from 0 to 150° C., preferably from 20 to 100° C.

In the fifth stage, the (1S,4R)- or (1R,4S)-4-[(2-amino-6-chloro-5-formamido-4-pyrimidinyl)amino]-2-cyclopentene- 1-methanol (formula IX, X) is cyclized in a known manner as disclosed in WO 95/21 161 to give the final product of the formula I or II.

The cyclization is normally carried out dissolved in trialkyl orthoformates in the presence of a concentrated aqueous acid. Examples of trialkyl orthoformates which can be used are trimethyl or triethyl orthoformate. It is possible to use as aqueous acid, for example, hydrochloric acid, sulphuric acid or methanesulphonic acid.

The invention further relates to a process for preparing the optically active compounds of the general formulae

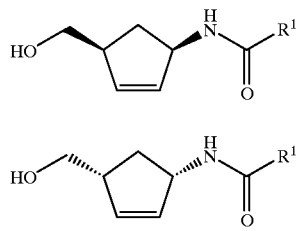

XVI

XVII in which $R^1$ has the stated meaning. These compounds can be obtained by converting a cyclopentene derivatives of the general formula

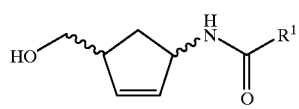

V in which $R^1$ has the state meaning, by means of the microorganisms, N-acetylamino-alcohol hydrolases or penicillin G acylases which have already been described previously into the (1R,4S)- or (1S,4R)-1-amino -4-(hydroxymethyl) -2-cyclopentene of the formulae

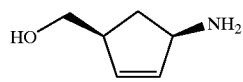

VI

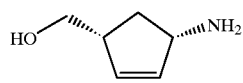

VII the latter being acylated to compounds of the formula XVI or XVII.

Both the microbiological conversion and the acylation are carried out under conditions which are per se the same as described previously.

This acylation is expediently carried out at a temperature from 20° C. or 100° C., preferably from 0° C. to 80° C.

Examples of optically active compounds which are prepared by this process are: (1R,4S)-N-tert-butoxy-carbonyl-1-amino-4-(hydroxymethyl)-2-cyclopentene with a ee of 98%, (1R,4S)-N-acetyl-1-amino-4-(hydroxymethyl)-2-cyclopentene with a ee of 98%, (1R,4S)-N-butyryl-1-amino-4-(hydroxymethyl)-2-cyclopentene with a ee of 98%, optically active (1S,4R)-N-acetyl-1-amino-4-(hydroxymethyl)-2-cyclopentene and optically active (1S,4R)-N-butyryl-1-amino-4-(hydroxymethyl)-2-cyclopentene.

Of these compounds, the optically active (1R,4S)-N-butyryl-1-amino-4-(hydroxymethyl)-2-cyclopentene is a compound which has not yet been described in the literature. Accordingly, the invention also relates to optically active (1R,4S)-N-butyryl-1-amino-4-(hydroxymethyl)-2-cyclopentene with an enantiomeric excess of more than 0%, preferably in an enantiomeric excess of at least 80%, 90% or 95%, in particular in an enantiomeric excess of at least 98%. These optically active compounds can be racemized in a manner known to the skilled person to give racemic N-butyryl- 1-amino-4-(hydroxymethyl)-2-cyclopentene which has not yet been described in the literature.

The process for preparing a racemic or optically active 4-(hydroxymethyl)-2-cyclopentene derivative of the general formula

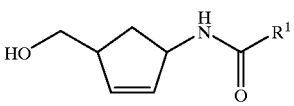

XIII in which $R^1$ has the stated meaning, is carried out by, in the first stage, acylating a cyclopentene-4-carboxylic acid of the formula

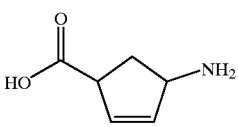

XIV in the form of a racemate or one of its optically active isomers, with a carbonyl halide of the general formula

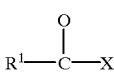

XI in which $R^1$ and X have the stated meaning, to give a racemic or optically active cyclopentene-4-carboxylic acid derivative of the general formula

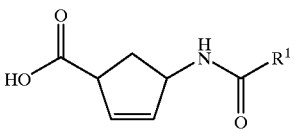

XV and, in the second stage, reducing the latter to the required product of the formula XIII.

Optically active 4-(hydroxymethyl)-2-cyclopentene derivatives (formula XIII) and optically active cyclopentene-4-carboxylic acid derivatives (formula XV) mean the corresponding (1R,4S), or (1S,4R) isomers.

The first stage of this process, the acylation, is carried out with a carbonyl halide of the general formula XI. The carbonyl halides which can be used are the same as described previously, and tert-butyloxy-carbonyl fluoride is preferably used.

The reaction in the first stage is expediently carried out at a pH from 8 to 14, preferably from 12 to 14, and at a temperature from 0 to 50° C., preferably from 15 to 25° C.

Suitable solvents are mixtures of water with ethers. Ethers which can be used are dioxane, tetrahydrofuran, diethyl ether, glycol dimethyl or diethyl ether.

The second state of the process, the reduction, can be carried out with an alkali metal aluminium hydride, with a borane/di-$C_{1-4}$-alkyl sulphide complex or with a borane/tetrahydrofuran complex. Lithium, sodium or potassium aluminium hydride can be used as alkali metal aluminium hydride, and lithium aluminium hydride is preferably used. Borane/dimethyl sulphide, borane/diethyl sulphide, borane/dipropyl sulphide or borane/dibutyl sulphide complexes can be used as borane/di-$C_{1-4}$-alkyl sulphide complex. Borane/dimethyl sulphide complex is preferably used.

It is expedient to use as solvent in the second stage one of the ethers mentioned above, without water.

The reaction in the second stage can be carried out at a temperature from −50 to 5° C., preferably from −25 to −10° C.

EXAMPLES

Example 1

Preparation of (±)-2-acetyl-2-azabicyclo[2.2.1]hept-5-en-3-one 100 g of (±)-2-azabicyclo[2.2.1]hept-5-en-3-one were dissolved in acetonitrile (800 ml) and pyridine (161.26 ml) under nitrogen. At 12° C., 104.5 g of acetyl chloride were added dropwise over the course of 2 hours. The mixture was then stirred at room temperature for 4.5 hours. 800 ml of water were added to the mixture, and the acetonitrile was evaporated off in vacuo. The aqueous phase was extracted 3 times with 400 ml of ethyl acetate. The combined org. phases were washed with 1N HCl (400 ml), water (400 ml), saturated NaCl (400 ml), dried with magnesium sulphate and completely evaporated. The residue was taken up in methylene chloride and filtered through silica gel. The filtrate was concentrated and the product was purified by distillation. 107.76 g of product were obtained as a clear liquid. The yield was 71%.

Boiling point (0.07 torr): 51° C.

| $^1$H-NMR (CDCl$_3$): δ [ppm] 400 MHz | 2.25 (AB syst., 2H); 2.8 (s, 3H); 3.42 (m, 1H); 5.30 (m, 1H); 6.89 (m, 1H); 6.92 (m, 1H); |
|---|---|

Example 2

Preparation of (±)-2-butyryl-2-azabicyclo[2.2.1]hept-5-en-3-one 100.3 g of (±)-2-azabicyclo[2.2.1]hept-5-en-3-one were dissolved in acetonitrile (720 ml) and pyridine (142 ml) under nitrogen. At 12° C., 141.8 g of butyryl chloride were added dropwise over the course of 1 hour. The reaction was then stirred at room temperature for 3 hours. 720 ml of water were added to the mixture, and the phases were separated. The acetonitrile was evaporated off in vacuo, and the aqueous phase was extracted 3 times with ethyl acetate (300 ml). The combined org. phases were washed with 1N HCl (350 ml), saturated NaCl (400 ml) and water (500 ml), dried with magnesium sulphate and completely evaporated. The product was purified by distillation. 107.76 g of product were obtained as a clear liquid. The yield was 85%.

Boiling point (0.05 torr): 70° C.

| $^1$H-NMR (CDCl$_3$): δ [ppm] 400 MHz | 0.98 (t, J = 8.5 Hz, 3H); 1.58–1.65 (2H); 2.23 (AB syst., 2H); 2.82–2.90 (2H); 3.42 (m, 1H); 5.30 (m, 1H); 6.62 (m, 1H); 6.90 (m, 1H). |
|---|---|

Example 3

Preparation of (±)-2-phenylacetyl-2-azabicyclo[2.2.1]hept-5-en-3-one 33.4 g of (±)-2-azabicyclo[2.2.1]hept-5-en-3-one were dissolved in acetonitrile (240 ml) and pyridine (48.3 ml) under nitrogen. At 12° C., 68.6 g of phenylacetyl chloride were added dropwise over the course of 30 minutes. The mixture was then stirred at room temperature for 3.5 hours. 240 ml of water were added to the mixture. The acetonitrile was evaporated off in vacuo, and the aqueous phase was extracted 3 time with ethyl acetate (150 ml). The combined org. phases were washed with 1N HCl (150 ml), saturated NaCl (150 ml) and water (150 ml), dried with magnesium sulphate and completely evaporated. The crude product was filtered through silica gel (hexane:ethyl acetate=1:1). 78.34 g of the crude product were obtained as a yellow oil.

Example 4

Preparation of (±)-2-propionyl-2-azabicyclo[2.2.1]hept-5-en-3-one 47 g of (±)-2-azabicyclo[2.2.1]hept-5-en-3-one were dissolved in acetonitrile (325 ml) and pyridine (41 ml) under nitrogen. At 12° C., 43.9 g of propionyl chloride were added dropwise over the course of 1 h. The reaction was then stirred at room temperature for 5 h. 145 ml of water were added to the mixture, and the acetonitrile was evaporated off in vacuo. The aqueous phase was extracted 3 times with 115 ml of ethyl acetate. The combined organic phases were washed with 1N HCl (140 ml), saturated NaHCO$_3$ (40 ml) and NaCl (40 ml) solutions, dried with sodium sulphate and completely evaporated. The residue was purified by distillation. 55.8 g of title compound were obtained and solidified on leaving to stand. The yield was 81.6%.

Boiling point 2.8 mbar 75–80° C.

Melting point: 54–56° C.

| $^1$H-NMR (DMSO-d$_6$): δ [ppm] 400 MHz | 0.95 (t, 3H); 2.10 (quart., 1H); 2.28 (quart., 1H); 2.64 (m, 2H); 3.42 (s, 1H); 5.16 (s, 1H); 6.78 (m, 1H); 6.96 (m, 1H). |
|---|---|

Example 5

Preparation of (±)-2-isobutyryl-2-azabicyclo[2.2.1]hept-5-en-3-one 45.1 g of (±)-2-azabicyclo[2.2.1]hept-5-en-3-one were dissolved in acetonitrile (310 ml) and pyridine (39 ml) under nitrogen. At 10° C., 54.1 g of isobutyryl chloride were added dropwise over the course of 1 h. The reaction was then stirred at room temperature for 5 h. 140 ml of water were added to the mixture, and the acetonitrile was evaporated off in vacuo. The aqueous phase was extracted with 4×120 ml of ethyl acetate. The combined organic phases were washed with 1N HCl (50 ml), saturated NaHCO$_3$ (50 ml) and NaCl (50 ml) solutions, dried with sodium sulphate and completely evaporated. The residue was boiled under reflux in n-hexane (240 ml) with active charcoal. After filtration of the active charcoal, the filtrate was cooled to 0° C. and the title compound was filtered. 54.5 g of produce were obtained. The yield was 76%.

Melting point: 41–42° C.

| $^1$H-NMR (DMSO-d$_6$): δ [ppm] 400 MHz | 0.92 (d, 3H); 1.06 (d, 3H); 2.10 (m, 1H); 2.28 (m, 1H); 3.40 (m, 2H); 5.16 (s, 1H); 6.78 (m, 1H); 7.92 (m, 1H). |
|---|---|

Example 6

Preparation of (±)-2-chloroacetyl-2-azabicyclo[2.2.1]-hept-5-en-3-one 10.1 g of (±)-2-azabicyclo[2.2.1]hept-5-en-3-one were dissolved in a mixture of dichloromethane (10 ml), pyridine (8.4 ml) and 0.22 g of 4-N,N-dimethylaminopyridine at 10° C. under nitrogen. 13.5 g of chloroacetyl chloride were added dropwise over the course of 1 h. The temperature rose to 44° C. The mixture was stirred for a further 2 h at room temperature. 100 ml of water were added to the solution. After phase separation, the aqueous phase was extracted with 100 ml of dichloromethane. The combined organic phases were dried with sodium sulphate and completely evaporated. The residue was boiled in 100 ml of diisopropyl ether under reflux in the presence of 1 g of active charcoal for 10 minutes. After hot filtration, the filtrate was cooled to room temperature, and the solid was filtered and dried. 10.35 g of title compound were obtained. The yield was 60%.

Melting point: 86–88° C.

| $^1$H-NMR (CDCl$_3$): δ [ppm] 400 MHz | 2.28 (d, 1H); 2.40 (d, 1H); 3.48 (s, 1H); 4.56 (d, 2H); 5.30 (s, 1H); 6.70 (d, 1H); 6.94 (m, 1H). |
|---|---|

Example 7

Preparation of (±)-1-acetylamino-4-(hydroxymethyl)-2-cyclopentene 79.56 g of (±)-2-acetyl-2-azabicyclo[2.2.1]hept-5-en-3-one were dissolved in ethanol (450 ml) under nitrogen and cooled to −10° C. 19.8 g of sodium borohydride were added in portions over the course of 45 minutes.

The reaction was stirred at 0° C. for 3 hours and then the pH was adjusted to 1.8 with conc. sulphuric acid. Ethyl acetate (200 ml) was added to this mixture, and the solids were filtered off. It was then completely evaporated. The residue was taken up in water, washed with methylene chloride and evaporated. The crude product was purified by a silica gel filtration. 51.83 g of produce were obtained as a white solid. The yield was 65% based on 2-acetyl-2-azabicyclo[2.2.1]hept-5-en-3-one employed.

| $^1$H-NMR (DMSO-d$_6$): δ [ppm] 400 MHz | 1.18 (m, 1H); 1.78 (s, 3H); 2.29 (m, 1H); 2.66 (m, 1H); 3.35 (s, 2H); 4.58 (s, 1H); 4.72 (m, 1H); 5.61 (d, 1H); 5.85 (d, 1H); 7.83 (d1 1H). |
|---|---|

Example 8

Preparation of (±)-1-butyrylamino-4-(hydroxymethyl)-2-cyclopentene 73.87 g of (±)-2-butyryl-2-azabicyclo[2.2.1]hept-5-en-3-one were dissolved in ethanol (400 ml) under nitrogen and cooled to −10° C. 15.68 g of sodium borohydride were added in portions over the course of 45 minutes. The reaction was stirred at 0° C. for 3 hours and then the pH was adjusted to 1.5 with conc. sulphuric acid. Ethyl acetate (200 ml) was added to this mixture, and the solids were filtered off. It was then completely evaporated. The residue was taken up in water, washed with methylene chloride, evaporated and dried under high vacuum. 60.55 g of product were obtained. The yield was 80% based on (±)-2-butyryl-2-azabicyclo[2.2.1]hept-5-en-3-one employed.

Melting point: 71–72° C.

| $^1$H-NMR (CDCl$_3$): δ [ppm] 400 MHz | 0.98 (t, J = 8.5 Hz, 3H); 1.40–1.50 (1H); 1.58–1.68 (2H); 2.10–2.18 (2H); 2.42–2.55 (1H); 2.85 (m, 1H); 3.62 (AB syst., 2H); 4.98 (m, 1H); 5.78–5.82 (2H); 6.38 (m, 1H). |
|---|---|

Example 9

Preparation of (±)-1-phenylacetylamino-4-(hydroxymethyl)-2-cyclopentene 77 g of crude (±)-2-phenylacetyl-2-azabicyclo-[2.2.1]hept-5-en-3-one were dissolved in ethanol (450 ml) under nitrogen and cooled to −10° C. 13.2 g of sodium borohydride were added in portions over the course of 1 hour. The reaction was stirred at room temperature for 3.5 hours and then the pH was adjusted to 1.8 with conc. sulphuric acid. This mixture was purified by a silica gel filtration (hexane:ethyl acetate=2:8). After recrystallization from ethyl acetate, 15.89 g of white solid were obtained. The yield was 80% based on (±)-2-phenylacetyl-2-azabicyclo[2.2.1]hept-5-en-3-one employed.

| ¹H-NMR (CDCl₃): δ [ppm] | 1.28–1.35 (1H); |
| --- | --- |
| 400 MHz | 1.40 (m, 1H); |
| | 2.38–2.45 (1H); |
| | 2.79 (m, 1H); |
| | 3.50 (AB syst., 2H); |
| | 3.52 (s, 3H); |
| | 4.98 (m, 1H); |
| | 5.75 (m, 2H); |
| | 5.98 (m, 1H). |
| | 7.20–7.38 (5H). |

Example 10

Preparation of (±)-1-BOC-amino-4-(hydroxymethyl)-2-cyclopentene (BOC=tert-butoxycarbonyl)

15 g of crude (±)-1-amino-4-hydroxymethyl-2-cyclopentene hydrochloride (prepared as described in J. Org. Chem. 1981, 46, 3628) were dissolved in a mixture of 150 ml of water and 150 ml of dioxane at room temperature under nitrogen. The solution was adjusted to pH 14 with 1N NaOH, then a diethyl ether solution of tert-butyloxycarbonyl fluoride (BOC-F, 20% excess) was added, and the mixture was stirred for a further 3 h at room temperature (BOC-F prepared as disclosed in Synthesis 1975, 599). The pH was adjusted to 2 with conc. HCl. After distillation of the organic solvents, 50 ml of water were added to the residue, and the mixture was extracted with 3×100 ml of ethyl acetate. The combined organic phases were completely evaporated. The residue was crystallized in a mixture of 110 ml of diisopropyl ether and 80 ml of n-hexane. 11.95 g of title compound were obtained. The yield was 56%.

Melting point: 68–70° C.

| ¹H-NMR (DMSO-d₆): δ [ppm] | 1.18 (m, 1H); |
| --- | --- |
| 400 MHz | 1.38 (s, 9H); |
| | 2.26 (m, 1H); |
| | 2.65 (m, 1H); |
| | 3.33 (t, 2H); |
| | 4.45 (m, 1H); |
| | 4.55 (t, 1H); |
| | 5.62 (m, 1H); |
| | 5.79 (m, 1H); |
| | 6.73 (d, 1H). |

Example 11

Preparation of (±)-1-propionylamino-4-(hydroxymethyl)-2-cyclopentene 16.6 g of (±)-2-propionyl-2-azabicyclo[2.2.1]-hept-5-en-3-one were dissolved in water (140 ml) and 2-butanol (66 ml) under nitrogen and cooled to −5° C. 3 g of sodium borohydride were added in portions over the course of 2 h. The mixture was stirred at 10° C. for 2.5 h and then adjusted to pH 2.2 with a mixture of conc. hydrochloric acid and water (1/1). The solution was evaporated to 40 g and adjusted to pH 6.2 with 2N NaOH. The mixture was extracted with 5×50 ml of dichloromethane. The combined organic phases were completely evaporated, and the residue was recrystallized in toluene (150 ml). 11.1 g of title compound were obtained. The yield was 65%.

Melting point: 67–68° C.

| ¹H-NMR (DMSO-d₆): δ [ppm] | 0.96 (t, 3H); |
| --- | --- |
| 400 MHz | 1.16 (quint., 1H); |
| | 2.04 (quart., 2H); |
| | 2.26 (m, 1H); |
| | 2.66 (m, 1H); |
| | 3.34 (m, 2H); |
| | 4.58 (t, 1H); |
| | 4.72 (m, 1H); |
| | 5.61 (m, 1H), |
| | 5.84 (m, 1H), |
| | 7.72 (d, 1H). |

Example 12

Preparation of (±)-1-isobutyrylamino-4-(hydroxymethyl)-2-cyclopentene 9 g of (±)-2-isobutyryl-2-azabicyclo[2.2.1]hept-5-en-3-one were dissolved in water (32 ml) and 2-butanol (84 ml) under nitrogen and cooled to 0° C. 1.37 g of sodium borohydride were added in portions over the course of 3.5 h. The mixture was stirred for a further 3 h at 20° C., and it was then adjusted to pH 2.5 with a mixture of conc. hydrochloric acid and water (1/1) and then neutralized with 2N NaOH. The solution was evaporated to 40 g. The residue was extracted with 3×80 ml of dichloromethane. The combined organic phases were completely evaporated. The resulting solid was crystallized in 25 ml of toluene. 6.8 g of title compound were obtained. The yield was 73.6%.

Melting point: 80–81° C.

| ¹H-NMR (DMSO-d₆): δ [ppm] | 0.98 (d, 6H); |
| --- | --- |
| 400 MHz | 1.16 (quint., 1H); |
| | 2.30 (m, 2H); |
| | 2.68 (m, 1H); |
| | 3.32 (t, 2H); |
| | 4.58 (t, 1H); |
| | 4.70 (m, 1H); |
| | 5.61 (m, 1H); |
| | 5.82 (m, 1H); |
| | 7.68 (d, 1H). |

Example 13

Preparation of (1R,4S)-1-amino-4-(hydroxymethyl)-2-cyclopentene using penicillin G acylases Penicillin G acylase EC 3.5.1.11 from *E. coli* (Boehringer Mannheim) 165 U (units)/g or penicillin G acylase EC 3.5.1.11 from *Bacillus megaterium* was employed for the biotransformation.

For this, 50 mM sodium phosphate buffer (pH 5–9; 4 ml) was incubated with 1% by weight of non-racemic 1-phenylacetylamino-4-hydroxymethyl-2-cyclopentene and 400 mg of the appropriate penicillin G acylase at 37° C.

Samples were taken after defined time intervals and were analyzed by thin-layer chromatography (silica gel 60, butanol:water:glacial acetic acid=3:1:1; detection with ninhydrin), gas chromatography (capillary column, HP-5, 5% phenylmethylsiloxane) or HPCL. The enzyme eliminated the phenylacetyl group with high activity and thereby liberated up to 40% of the corresponding amino alcohol. The free amino alcohol was obtained with a ee of 80%.

Example 14

Preparation of (1R,4S)-1-amino-4-(hydroxymethyl)-2-cyclopentene using microorganisms 14.1 Sewage sludge (20%) from the ARA water treatment plant in Visp was incubated in the A+N medium (see Table 1) containing 0.5% by weight of 1-acetyl-, 1-propionyl-, 1-isobutyryl- or 1-butyrylamino-4-hydroxymethyl-2cyclopentene at 37° C. with shaking. The formation of (1R,4S)-1-amino-4-(hydroxymethyl)-2-cyclopentene was followed by thin-layer chromatography.

1–3 transfers were carried out with 1% of these enrichments, and isolation took place on solid media (plate count agar in the medium of Table 1; 20 g/l). The microorganisms Alcaligenes/Bordetella FB 188 (DSM 1172), *Rhodococcus erythropolis* CB 101 (DSM 10686), Gordona sp. CB 100 (DSM 10687) and Rhodococcus sp. FB 387 (DSM 11291) were isolated in this way.

14.2 The microorganisms isolated in this way were cultivated in the medium (Table 1) containing 0.5% of 1-acetyl-, 1-propionyl-, 1-isobutyryl- or 1-butyrylamino-4-hydroxymethyl-2-cyclopentene. They grew to an optical density (OD) of 2 to 3 in 24 to 36 hours. The cells obtained in this way were harvested in the late exponential phase of growth and were washed in 10 mM phosphate buffer.

The subsequent biotransformation was carried out in 50 mM phosphate buffer (pH 4.5–9) containing 1% by weight of 1-acetyl-, 1-isobutyryl- or 1-butyrylamino-4-hydroxymethyl-2-cyclopentene. It was found by thin-layer chromatography that 50% of the substrate were hydrolyzed to (1R,4S)-1-amino-4-(hydroxymethyl)-2-cyclopentene. HPLC analyses revealed ee values between 80 and 93%.

When 1-butyrylamino-4-hydroxymethyl-2-cyclopentene was employed as substrate, the biotransformation rate was 0.14 (g/l/h/OD) for the strain DSM 10686 when cultivation took place on a A+N medium and 0.03 (g/l/h/OD) when cultivation took place on NYB (nutrient yeast broth) medium containing 1-butyrylamino-4-hydroxymethyl-2-cyclopentene.

When the same conversion was carried out with the strain DSM 10687 at a substrate concentration (1-butyrylamino-4-hydroxymethyl-2-cyclopentene) of 200 mM, the biotransformation rate was 0.161 (g/l/h/OD).

TABLE 1

| A + N medium | |
|---|---|
| $MgCl_2$ | 0.4 g/l |
| $CaCl_2$ | 0.014 g/l |
| $FeCl_3$ | 0.8 mg/l |
| $Na_2SO_4$ | 0.1 g/l |
| $KH_2PO_4$ | 1 g/l |
| $Na_2HPO_4$ | 2.5 g/l |
| NaCl | 3 g/l |
| Vitamin solution | 1 ml/l |
| Trace element solution | 1 ml/l |
| pH | 7.5 |

14.3 *Rhodococcus erythropolis* DSM 10686 was cultured in minimal medium (cf. Table 2) with ammonium acetate (3 g/l) as carbon and nitrogen source in a 6 l fermenter at 30° C. to a cell density of OD 650>25. During cell growth, 50% acetic acid was added continuously as additional C source. In order to induce the enzymatic activity, 60 g of (±)-1-acetylamino-4-hydroxymethyl-2-cyclopentene were then added, and incubation was continued for some hours. Finally, a further 40 g of (±)-1-acetylamino-4-hydroxymethyl-2-cyclopentene were added, and incubation was then carried out for a further 10 hours. The progress of the biotransformation was followed on-line by HPLC. When an analytical yield of 40%, based on the racemic substrate employed, and a ee of 85% were reached, fermentation was stopped by adding acid.

TABLE 2

| Media composition | |
|---|---|
| Component | Concentration |
| Yeast extract | 0.5 g/l |
| Peptone M66 | 0.5 g/l |
| $KH_2PO_4$ | 4.0 g/l |
| $Na_2HPO_4 2H_2O$ | 0.5 g/l |
| $K_2SO_4$ | 2.0 g/l |
| $NH_4$ acetate | 3.0 g/l |
| $CaCl_2$ | 0.2 g/l |
| $MgCl_2.6H_2O$ | 1.0 g/l |
| Trace element solution (see below) | 1.5 ml/l |
| PPG (polypropylene glycol) | 0.1 g/l |
| Trace element solution | |
| KOH | 15.1 g/l |
| $EDTA.Na_2.2H_2O$ | 100.0 g/l |
| $ZnSO_4.7H_2O$ | 9.0 g/l |
| $MnCl_2.4H_2O$ | 4.0 g/l |
| $H_3BO_3$ | 2.7 g/l |
| $CoCl_2.6H_2O$ | 1.8 g/l |
| $CuCl_2.2H_2O$ | 1.5 g/l |
| $NiCl_2.6H_2O$ | 0.18 g/l |
| $Na_2MoO_4.2H_2O$ | 0.27 g/l |

14.4 In analogy to Example 14.3, the microorganisms Arthrobacter sp. HSZ 5 (DSM 10328, Rhodococcus sp. FB387 (DSM 11291), *Alcaligenes xylosoxydans* ssp. denitrificans HSZ 17 (DSM 10329), Agrobacterium/Rhizobium HSZ 30, *Bacillus simplex* K2 and *Pseudomonas putida* K32 were cultured on sodium acetate in the medium (Table 1) with and without 1-acetyl-, 1-propionyl-, 1-isobutyryl- or 1-butyrylamino-4-hydroxymethyl-2-cyclopentene, abbreviated to amino alcohols hereinafter.

The following results were obtained with exponential cells cultured without amino alcohols (HPLC analysis):

| Strain | Rate [mmol/OD.h] | ee/conversion [%] |
|---|---|---|
| HSZ 5 (DSM 10328) | 0.05 | 88.7/16 |
| HSZ 17 (DSM 10329) | 0.005 | 95/23 |
| K32 | 0.05 | 54/1 |
| CB101 (DSM 10686) | 0.1 | 84/39 |

The strains K2 and K17 were cultured, harvested and subjected to a 60-hour biotransformation.

| Strain | Rate [mmol/OD.h] | ee/conversion [%] |
|---|---|---|
| K2 | — | 92/10 |
| HSZ 30 | — | 93/3.5 |

Exponential and stationary cells were harvested from all the batches and employed as quiescent cells for the biotransformation. There was no observable difference, from the TLC analysis, in the initial rate of cells induced with amino alcohol or not induced.

Example 15

Purification of the N-Acetylamino-Alcohol Hydrolase from *Rhodococcus Erythropolis* CB101 (DSM 10686)

The enzyme was purified as described below until there was only one protein band in the SDS-PAGE (Pharmacia Phast gel, 10–15% gradient) at a molecular weight of 50 kD.

Cells of *Rhodococcus erythropolis* CB101 (DSM 10686) were washed in 50 mM tris buffer (pH 6.2) and concentrated to an optical density $OD_{650\ nm}$ of 190. After addition of phenylmethanesulphonyl fluoride (PMSF) to a final concentration of 1 mM and DNAse, the cells were treated with a French press in order to obtain a crude extract. Centrifugation resulted in 200 ml of a cell-free extract with a protein concentration of 4.8 mg ml$^{-1}$.

960 mg of the cell-free extract were loaded onto a HiLoad 26/10 Q-Sepharose ion exchange chromatography column (Pharmacia) which had ben equilibrated with a 50 mM tris buffer (pH 8.0) containing 1 mM dithiothreitol (DTT).

After the column had been washed with the same buffer, the proteins were eluted with a linear buffer gradient (1500 ml; gradient: 50 mM tris buffer (pH 8.0) containing 1 mM DTT—50 mM tris buffer (pH 7.0) containing 1 mM DTT and 1 M NaCl). The enzyme eluted from the column between 370 and 430 mM NaCl and at a pH of 7.6. The active fractions were collected and concentrated to 9 mol. The protein content was 41 mg.

For further purification, the protein solution was loaded onto a HiLoad 26/60 Superdex 75 gel filtration chromatography column (Pharmacia) which had been equilibrated with a 50 mM tris buffer containing 50 mM NaCl and 1 mM DTT. The active fractions were combined and had a total protein content of 10.9 mg.

This protein solution was loaded onto a Mono Q HR5/5 column (Pharmacia) which had been equilibrated with 50 mM tris buffer (pH 8.5) containing 1 mM DTT. The proteins were eluted with a linear gradient (40 ml) of 50 mM tris buffer (pH 8.5) containing 1 mM DTT—50 mM tris buffer (pH 8.5) containing 1 mM DTT and 1 M NaCl. The enzyme eluted between 390 mM NaCl and 440 mM NaCl. The active fractions contained 1.4 mg of protein.

In the last purification step, the same column was used, equilibrated with the same buffer. The elution gradient used was the same buffer with 0–500 mM NaCl and pH 7.0–8.5. It was possible in this way to isolate 430 μg of pure enzyme.

The N-terminal sequence of the enzyme was determined directly from the protein blot. A sequence of the following 20 amino acids was obtained: Thr-Glu-Gln-Asn-Leu-His-Trip-Leu-Ser-Ala-Thr-Glu-Met-Ala-Ala-Ser-Val-Ala-Ser-Asn.

This sequence showed no homology with known proteins.

Example 16

Enzyme characterization

The enzyme characterization was carried out both with purified enzyme and with cell-free extract which had been desalted using a Sephadex G-25 column (PD-10, Pharmacia).

The protein concentration in the cell-free extract was 7.3 mg ml$^{-1}$ and the protein concentration of the purified enzyme was 135 μg ml$^{-1}$. PMSF was not added to the cell-free extract.

16.1 $K_m$ determination

The $K_m$ determination was carried out in a cell-free extract. The $K_m$ for the reaction at pH 7.0 and at a temperature of 30° C. was 22.5 mM for the substrate 1-acetylamino-4-hydroxymethyl-2-cyclopentene.

16.2 pH optimum

The pH optimum for the hydrolysis of 1-acetylamino-4-hydroxymethyl-2-cylopentene (25 mM) was determined with the purified enzyme and in cell-free extract in a pH range of pH 6.2–9.0 in the following buffer solutions.

Tris buffer 100 mM pH 9.0; 8.5; 8.0; 7.5; 7.0 Citrate/phosphate buffer 100 mM pH 7.0; 6.55; 6.2

The activity was measured for 24 h. The pH optimum for the reaction was between pH 7.0 and pH 7.5 for production of the 1R, 4 S and the 1 S, 4R enantiomer.

The pH optimum for the activity in the cell-free extract was at pH 7.0. The selectivity was, however, better between pH 6.09 and pH 7.0.

Figure 1:
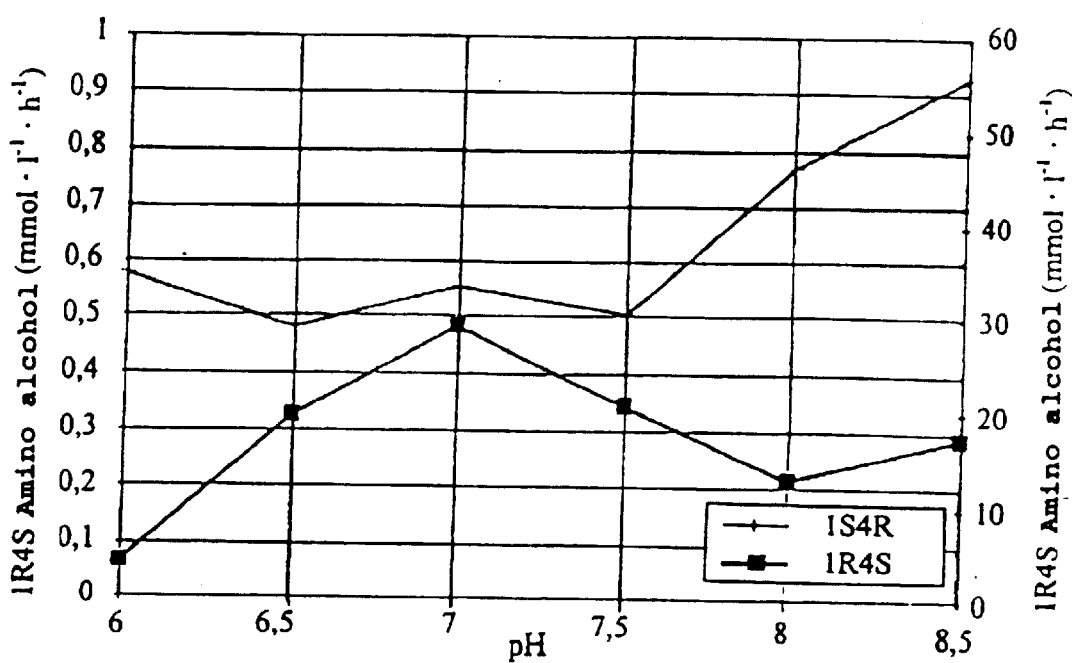
FIG. 1 shows the activity of the N-acetylamino-alcohol hydrolase (cell-free extract) from Rhodococcus erythropolis CB 101 (DSM 10686) as a function of the pH. The temperature optimum for the reaction indicated in Example 16.2 was between 25 and 30° C.
Figure 2:
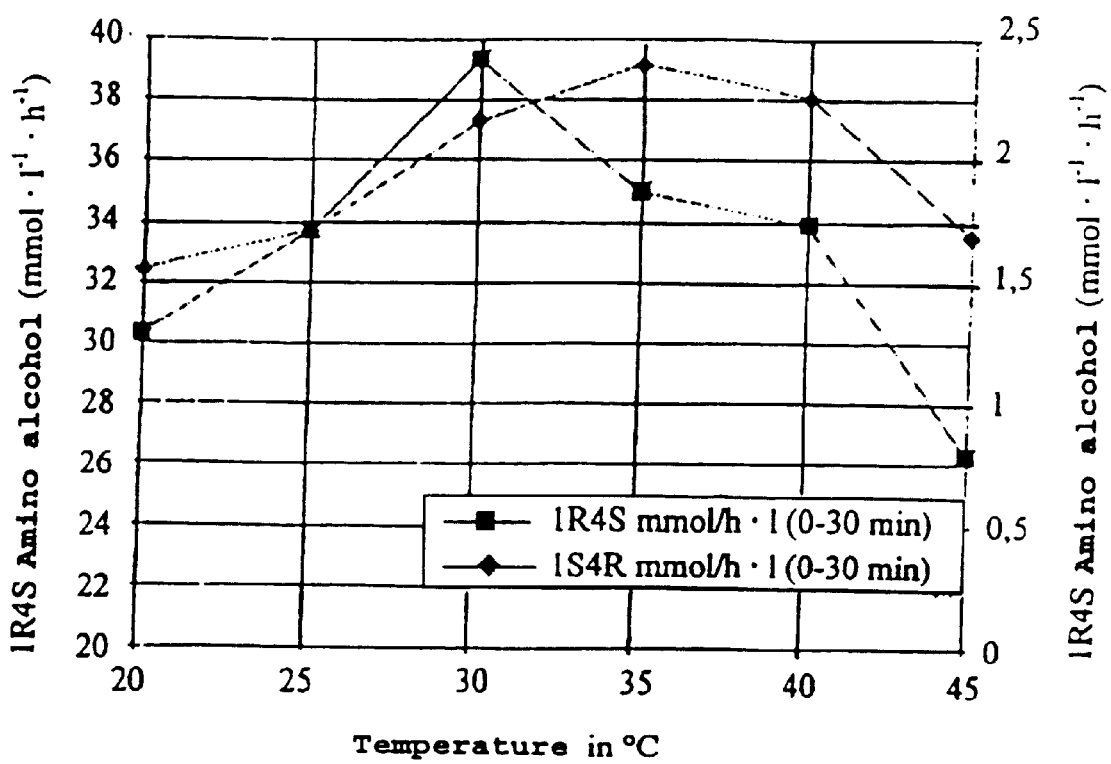
FIG. 2 shows the activity of the N-acetylamino-alcohol hydrolase (cell-free extract) from Rhodococcus erythropolis CB 101 (DSM 10686) as a function of the temperature.

16.4 The molecular weight was determined by SDS-PAGE to be 50 kD.

16.5 The following substrates were hydrolyzed: 1-acetyl-amino-4-hydroxymethyl-2-cyclopentene, 1-butyryl-amino-4-hydroxymethyl-2-cyclopentene, 1-propionyl-amino-4-hydroxymethyl-2-cyclopentene, 1-isobutyryl-amino-4-hydroxymethyl-2-cyclopentene.

Example 17

Preparation of (1R, 4 S)-1-amino-4-(hydroxymethyl)-2-cylopentene hydrochloride 374.1 g of a solution of (1R, 4 S)-1-amino-4-hydroxymethyl-2-cylopentene (preparation similar to that in Example 14) were evaporated to 123.7 g. The solution contained 60.2 mmol of the above compound (HPLC) and was adjusted from pH 2 to pH 11.7 with 30% strength NaOH and then extracted with 3×70 ml of isobutanol. The combined isobutanol extracts were adjusted to pH 1 with gaseous Hcl, concentrated to 65 g and filtered (removal of solid impurities). 60 ml of acetone were added dropwise to the vigorously stirred filtrate at 20° C. The cloudy mixture was seeded with crystals of the title compound and stirred at 5° C. for 1 h. Filtration and drying resulted in 5.2 g of product. The yields was 58%.

Melting point: 125–127° C.

ee 98% (calibrated chiral HPLC column)

| $^1$H-NMR (DMSO-d$_6$): δ [ppm] 400 MHz | 1.44 (m, 1H); 2.35 (m, 1H); 2.83 (m, 1H); 3.42 (m, 2H); 4.10 (s, 1H); 4.60 (s, 1H); 5.80 (d, 1H); 6.06 (d, 1H); 8.13 (s, 3H). |
|---|---|

Example 18

Preparation of (1R, 4 S)-1-BOC-amino-4-(hydroxymethyl)-2-cylopentene 75 g of a solution of (1R, 4 S)-1-amino-4-hydroxy-methyl-2-cyclopentene (preparation similar to that in Example 14; 44.6 mmol of the compounds) were adjusted to pH 8 with 30% strength NaOH, and 6 g of NaHCO$_3$ were added. The mixture was heated to 52° C. While stirring vigorously, 60 ml of diisopropyl ether were added and then a solution of 11.12 g of BOC anhydride in 18.2 ml of diisopropyl ether was metered in over the course of 2 h. The mixture was filtered through Celite, and the phases were separated. The aqueous phase was extracted with 65 ml of diisopropyl ether. The combined organic phases were washed with 45 ml of water and then evaporated to 37.5 g and heated to 50° C. 31 ml of n-hexane were added dropwise to the solution. After slowly cooling to 0° C. (2 h), the title compound was filtered, washed with 12 ml of n-hexane/diisopropyl ether ¼ and dried. 6.75 g of product were obtained. The yield was 71%.

Melting point: 70–71° C.

ee 98% (calibrated chiral HPLC column)

| $^1$H-NMR (DMSO-d$_6$): δ [ppm] 400 MHz | 1.18 (m, 1H); 1.27 (s, 9H); 2.28 (m, 1H); 2.63 (m, 1H); 3.33 (q, 2H); 4.43 (m, 1H); 4.56 (t, 1H); 5.62 (m, 1H); 5.78 (m, 1H); 6.72 (d, 1H). |
|---|---|

Example 19

Preparation of (1R, 4 S)-1-amino-4-(hydroxymethyl)-2-cyclopentene hydrochloride 87.8 g of (1R, 4 S)-1-BOC-amino-4-hydroxymethyl-2-cyclopentene were dissolved in 270 ml of 2 N HCl and 1340 ml of methanol. The mixture was boiled under reflux for 4.5 h. After distillation of the methanol, the residue was dissolved in 800 ml of water. The aqueous solution was extracted twice with 340 ml of ethyl acetate. The aqueous phase was completely evaporated (50° C./60 mbar). The solid was dried at 50° C. in vacuo, suspended in 150 ml of diethyl ether, filtered off and washed twice with 50 ml of diethyl ether. Drying resulted in the title compound in a yield of 95% (58.4 g).

The physical and spectroscopic data of the product were the same as in Example 17.

Example 20

Preparation of (1R, 4 S)-1-acetylamino-4-(hydroxymethyl)-2-cyclopentene 25 g of (1R, 4 S)-1- amino-4-(hydroxymethyl)-2-cyclopentene hydrochloride were dissolved in 182 ml of acetic anhydride and, at 0° C., a solution of 18.25 g of triethylamine in 60 ml of acetic anhydride was added. The mixture was stirred at 80° C. for 3 h and then cooled to room temperature. The triethylamine hydrochloride was filtered off and washed with 120 ml of n-hexane. The filtrate was evaporated. The residue was mixed with 300 ml of toluene and stirred at room temperature in the presence of 5.2 g of active charcoal and 13 g of Celite for 20 min. After filtration and washing of the filter cake (3×40 ml of toluene), the solvent was completely evaporated off. The residue was mixed with 180 ml of methanol and 15.5 g of K$_2$CO$_3$ and stirred at room temperature for 10 h. The suspension was filtered and the filtrate was evaporated. The residue was suspended in 750 ml of isopropyl acetate and boiled in the presence of 0.5 g of active charcoal under reflux for 1.5 h. After the active charcoal filtration (70–80° C.), the filtrate was cooled at 0° C. overnight. The title compound was filtered, washed with 80 ml of cold isopropyl acetate and dried in vacuo. 17.2 g of product were obtained. The yield was 66%.

Melting point: 77–80° C.

ee 98% (calibrated chiral HPLC column)

| $^1$H-NMR (DMSO-d$_6$): δ [ppm] 400 MHz | 1.15 (m, 1H); 1.78 (s, 3H); 2.25 (m, 1H); 2.66 (m, 1H); 3.35 (m, 2H); 4.58 (t, 1H); 4.70 (m, 1H); 5.62 (m, 1H); 5.85 (m, 1H); 7.80 (d, 1H). |
|---|---|

Example 21

Preparation of (1 S, 4R)-1-acetylamino-4-(hydroxymethyl)-2-cyclopentene

It was possible to prepare the title enantiomer by the process of Example 18 starting from 25 g of (1 S, 4R)-1-amino-4-hydroxymethyl-2-cyclopentene hydrochloride (yield 68%). The spectroscopic and physical data of the product were the same as in Example 20.

Example 22

Preparation of (1R, 4 S)-1-butyrylamino-4-(hydroxymethyl)-2-cyclopentene 34.7 g of (1R, 4 S)-1-amino-4-hydroxymethyl-2-cyclopentene hydrochloride and 2 g of 4-N,N-dimethylaminopyridine were dissolved in 600 ml of methylene chloride. The solution was cooled to 0° C. Then 52 g of triethylamine were added dropwise (5 min). The mixture was stirred at 0° C. over the course of 1 h. The mixture was stirred for a further 1.5 h at between 0 and 20° C., and then 600 ml of water were added. After phase separation, the aqueous phase was extracted with 600 ml of methylene chloride. The combined organic phases were washed 3 times with 500 ml of 10% strength NaOH each time, and then completely evaporated. The dried solid was dissolved in 120 ml of methanol. The solution was mixed with 5 g of K$_2$CO$_3$ and stirred for a further 2 h at room temperature. The inorganic salts were filtered off and washed with 20 ml of methanol. The filtrate was neutralized with 2 N HCl. The suspension was filtered and the filter cake was washed with 20 ml of methanol. The filtrate was completely evaporated. The solid residue was dried and crystallized in 150 ml of toluene. 28.5 g of title compound were obtained. The yield was 67%.

Melting point: 71–72° C.

ee 98% (calibrated chiral HPLC column)

| $^1$H-NMR (DMSO-d$_6$): δ [ppm] 400 MHz | 0.85 (t, 3H); 1.15 (m, 1H); 1.50 (q, 2H); 2.03 (d, 2H); 2.28 (m, 1H); 2.67 (m, 1H); |
|---|---|

| | |
|---|---|
| | 3.35 (d, 2H); |
| | 4.62 (s, 1H); |
| | 4.76 (m, 1H); |
| | 5.63 (m, 1H); |
| | 5.85 (m, 1H); |
| | 7.77 (d, 1H). |

Example 23

Preparation of (1 S, 4R)-1- butyrylamino-4-(hydroxymethyl)-2-cyclopentene

It was possible to prepare the title enantiomer by the method of Example 20 starting from 34.7 g of (1S, 4R)-1-amino-4-hydroxymethyl-2-cyclopentene hydrochloride (yield 63%). The spectroscopic and physical data of the product were the same as in Example 22.

Example 24

Preparation of (1R, 4 S)-1-[(2-amino-6-chloro-5-formamido-4-pyrimidinyl) amino]-4-(hydroxymethyl)-2-cylopentene 2.07 g of N-(2-amino-4,6-dichloro-5-pyrimidinyl) formamide were heated to 80° C. in 40 ml of isobutanol (white suspension). A solution of 1.97 g of (1R, 4 S)-1-amino-4-(hydroxymethyl)-2-cyclopentene hydrochloride, 3.8 g of triethylamine and 15 ml of isobutanol was added to the mixture. The mixture was stirred at 80° C. for a further 13 h. 10 ml of 1 N NaOH were added to the clear solution at 20° C., followed by evaporation to dryness. The residue underwent flash chromatography (silica gel 60 column, length 8 cm, diameter 6.5 cm, eluent ethyl acetate/methanol 95/5). After evaporating off the eluent and drying the residue, 2.1 g of title compound were obtained. The yield was 74%.

Melting point: 174–176° C.

ee 98% (calibrated chiral HPLC column)

| $^1$H-NMR (DMSO-$d_6$): δ [ppm] 400 MHz | 1.37 (m, 1H); |
|---|---|
| | 2.35 (m, 1H); |
| | 2.73 (m, 1H); |
| | 3.38 (t, 2H); |
| | 4.68 (m, 1H); |
| | 5.08 (m, 1H); |
| | 5.70 (d, 1H); |
| | 5.85 (d, 1H); |
| | 6.40; 6.55 and 6.65 (s, d and d, together 3H); |
| | 7.78 and 8.10 (d and s, together 1H); |
| | 8.55 and 8.95 (d and s, together 1H). |

Example 25

Preparation of (1R, 4 S)-1-[(2-amino-6-chloro-5-formamido-4-pyrimidinyl) amino]-4-(hydroxymethyl)-2-cyclopentene 145.2 ml of a solution of (1R, 4 S)-1-amino-4-hydroxymethyl-2-cylopentene (preparation similar to that in Example 14) were concentrated to 25.5 ml and filtered through Celite. The filter cake was washed with 7.5 ml of water. The filtrate contained 17.7 mmol of the above compound (HPLC) and was adjusted from pH 6.6 to pH 1 with conc. HCl and then extracted 3 times with 20 ml of isobutanol. The organic phase was discarded. The aqueous phase was adjusted to pH 12 with 30% strength NaOH and extracted 3 times with 10 ml of isobutanol. The combined organic phases were evaporated to 15 ml and 2.53 g of triethylamine were added. A solution of 2.07 g of N-(2-amino-4, 6-dichloro-5-pyrimidinyl) formamide in 40 ml of ethanol was added to the mixture as in Example 24. The mixture was stirred at 80° C. for 16 h. Working up as in Example 22 resulted in 2.4 g of title compound. The yield was 85%.

The physical and spectroscopic data of the product were the same as in Example 24.

Example 26

Preparation of (±)-1-BOC-amino-2-cyclopentene-4-carboxylic acid 16.4 g of crude (±)-1-amino-2-cyclopentene-4-carboxylic acid hydrochloride (prepared as in J. Org. Chem. 1981, 46, 3268) were dissolved in a mixture of 80 ml of water and 80 ml of dioxane at room temperature under nitrogen. The mixture was then adjusted to pH 14 with 1 N NaOH, and a diethyl ether solution of tert-butyloxycarbonyl fluoride (BOC-F, 20% excess) was added (BOC-F prepared as in Synthesis 1975, 599). .The mixture was stirred for a further 5 h at room temperature. The pH was adjusted to 2 with conc. HCl. After distillation of the organic solvents, 50 ml of water were added to the residue, and the mixture was extracted 3 times with 100 ml of ethyl acetate. The organic phase was evaporated to 50 ml and diluted with 25 ml of toluene. After cooling (0–10° C.), the title compound was filtered and dried. 14.3 g of product were obtained. The yield was 63%.

Melting point: 126–127° C.

| $^1$H-NMR (DMSO-$d_6$): δ [ppm] 400 MHz | 1.14 (s, 9H); |
|---|---|
| | 1.70 (m, 1H); |
| | 2.40 (m, 1H); |
| | 3.40 (m, 1H); |
| | 4.47 (m, 1H); |
| | 5.70 (t, 1H); |
| | 4.87 (t, 1H); |
| | 6.88 (d, 1H); |
| | 12.30 (d, 1H). |

Example 27

Preparation of (±)-1-BOC-amino-4-(hydroxymethyl)-2-cyclopentene from (±)-1-BOC-amino-2-cyclopentene-4-carboxylic acid 250 ml of tetrahydrofuran and 10.02 g (0.164 mol) of LiAlH$_4$ were introduced into a 500 ml stirring apparatus, and a solution of 30.0 g (0.132 mol) of (±)-1-BOC-amino-2-cyclopentene-4-carboxylic acid in 75 ml of tetrahydrofuran was metered in at −10° C. over the course of 1 h. Then 10 g of water, 10 g of 15% strength NaOH solution and 20 g of water were added, followed by filtration. The residue was washed twice with 100 ml of tert-butyl methyl ether each time, and the combined organic phases were evaporated to dryness. After addition of 80 ml of hexane and seeding with the compound of Example 10, the title compound separated out as crystalline solid. Yield 15.84 g (56%). The physical and spectroscopic data were the same as in Example 10.

Example 28

Preparation of (1R, 4S)-1-BOC-amino-4-(hydroxymethyl)-2-cyclopentene from (1R, 4S)-1-BOC-amino-2-cyclopentene-4-carboxylic acid 80 ml of tetrahydrofuran and 11.38 g (50.07 mmol) of (1R, 4S)-1-BOC-amino-2-cyclopentene-4-carboxylic acid (prepared as in Tetrahedron: Asymmetry 1993, 4, 1117) were introduced into a 500 ml stirring apparatus, and 5 ml of borane/dimethyl sulphide complex were metered in at −15° C. over the course of 1 h, and the mixture was then stirred at this temperature for 3 h. A solution of 4 g of NaOH in 60 ml of water was added and warmed to room temperature. Extraction with toluene, filtration through silica gel and subsequent crystallization in ethyl acetate/n-hexane 1:1 afforded 5.4 g of the title compound, corresponding to a yield of 57%, as a white crystalline solid. The physical and spectroscopic data were the same as in Example 10. The ee was 99% (same chiral HPLC column).

What is claimed is:

1. Process for the preparation of an enantiomer of a (1R, 4S)- or (1S, 4R)-1-amino-4-(hydroxymethyl)-2-cyclopentene derivative of the general formulae

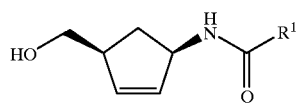

XVI

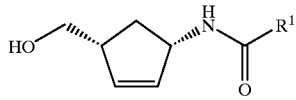

XVII wherein $R^1$ is an unsubstituted or halogen-substituted $C_{1-4}$-alkyl, a $C_{1-4}$-alkoxy, an aryl or an aryloxy, characterized in that in the first stage a cyclopentene derivative of the general formula,

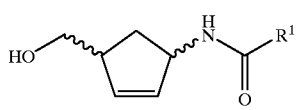

V is converted using a microorganism which is able to utilize a cyclopentene derivative of the general formula V as sole nitrogen source, as sole carbon source or as sole carbon and nitrogen source, an enzyme having N-acetylamino-alcohol hydrolase activity or a penicillin G acylase into the (1R, 4S)- or (1S, 4R)-1-amino-4-(hydroxymethyl)-2-cyclopentene of the formulae and the latter is then acylated in the second stage to give the compounds of the formula XVI or XVII.

* * * * *

UNITED STATES PATENT AND TRADEMARK OFFICE
CERTIFICATE OF CORRECTION

PATENT NO.     : 6,252,112 B1
DATED          : June 26, 2001
INVENTOR(S)    : Bernegger et al.

It is certified that error appears in the above-identified patent and that said Letters Patent is hereby corrected as shown below:

Title Page,
Item [54], Title, "(1R,4S)" should read -- (1R,4S)- --
Item [57], ABSTRACT,
Line 3, "formula" should read -- formulae --
Item [73], Assignee, "A.G.,," should read -- A.G., --
Item [75], Inventor(s), "Kurt" should read -- Knut --

Column 1,
Line 2, "(1R,4S)" should read -- (1R,4S)- --
Line 46, "9yl" should read -- 9-yl --
Line 50, "9yl" should read -- 9-yl --

Column 3,
Line 18, "stating" should read -- stated --

Column 4,
Line 10, "a" (second occurrence) should read -- or --
Line 59, "Midroorganismen" should read -- Mikroorganismen --

Column 6,
Line 61, "Peptidoglky-" should read -- Peptidogly- --

Column 7,
Line 52, "Maximum temperature" should read -- <u>Maximum temperature</u> --

Column 11,
Line 34, "state" should read -- stated --
Line 59, "a" should read -- an --
Line 61, "a" should read -- an --
Line 62, "a" should read -- an --

Column 12,
Line 56, "(1R,4S)," should read -- (1R,4S) --

Column 15,
Line 11, "produce" should read -- product --

UNITED STATES PATENT AND TRADEMARK OFFICE
CERTIFICATE OF CORRECTION

PATENT NO. : 6,252,112 B1
DATED : June 26, 2001
INVENTOR(S) : Bernegger et al.

It is certified that error appears in the above-identified patent and that said Letters Patent is hereby corrected as shown below:

<u>Column 16,</u>
Line 5, "produce" should read -- product --

<u>Column 18,</u>
Line 1, "a" should read -- an --
Line 64, "-(hydroxymethyI)-" should read -- -(hydroxymethyl)- --

<u>Column 19,</u>
Line 3, "2cyclopentene" should read -- 2-cyclopentene --

<u>Column 21,</u>
Line 11, "ben" should read -- been --
Line 42, "Trip-" should read -- Trp- --
Line 65, "-cylopentene" should read -- -cyclopentene --

<u>Column 22,</u>
Line 3, "The" should read -- ¶The --
Line 5, "4 S" should read -- 4S --; and "1 S" should read -- 1S --
Line 29, "-cylopentene" should read -- -cyclopentene --
Line 37, "Hcl" should read -- HCl --
Line 59, "4 S" should read -- 4S --
Line 60, "-cylopentene" should read -- -cyclopentene --
Line 62, "4 S" should read -- 4S --

<u>Column 23,</u>
Line 29, "4 S" should read -- 4S --
Line 32, "4 S" should read -- 4S --
Line 47, "4 S" should read -- 4S --
Line 50, "4 S" should read -- 4S --

<u>Column 24,</u>
Line 22, "1 S" should read -- 1S --
Line 26, "1 S" should read -- 1S --
Line 33, "4 S" should read -- 4S --
Line 36, "4 S" should read -- 4S --

UNITED STATES PATENT AND TRADEMARK OFFICE
CERTIFICATE OF CORRECTION

PATENT NO.   : 6,252,112 B1
DATED        : June 26, 2001
INVENTOR(S)  : Bernegger et al.

It is certified that error appears in the above-identified patent and that said Letters Patent is hereby corrected as shown below:

Column 25,
Line 13, "1 S" should read -- 1 S --
Line 23, "4 S" should read -- 4S --
Line 25, "-cylopentene" should read -- -cyclopentene --
Line 28, "4 S" should read -- 4S --
Line 32, "1 N" should read --1N --
Line 35, "eluent" should read -- eluant --
Line 36, "eluent" should read -- eluant --
Line 60, "4 S" should read -- 4S --
Line 65, "-cylopentene" should read -- -cyclopentene --

Column 26,
Line 24, "1 N" should read --1N --

Column 28,
Line 11, "formula," should read -- formula --
Line 27, "formulae and" should read -- formulae  and --

Signed and Sealed this

Twelfth Day of November, 2002

*Attest:*

*Attesting Officer*

JAMES E. ROGAN
*Director of the United States Patent and Trademark Office*